United States Patent
Brown et al.

(10) Patent No.: US 11,612,434 B2
(45) Date of Patent: Mar. 28, 2023

(54) SIDE-FIRE LASER SYSTEM WITH STAND-OFF CATHETER, STANDOFF CATHETER, AND METHOD OF USING SURGICAL LASER TO ACHIEVE BOTH TISSUE VAPORIZATION AND RAPID COAGULATION TO PREVENT OR HALT BLEEDING

(71) Applicants: Joe D. Brown, Panama City Beach, FL (US); Howard S. Klymas, Panama City Beach, FL (US); Daniel Malphurs, Panama City Beach, FL (US)

(72) Inventors: Joe D. Brown, Panama City Beach, FL (US); Howard S. Klymas, Panama City Beach, FL (US); Daniel Malphurs, Panama City Beach, FL (US)

(73) Assignee: Optical Integrity, Inc, Panama City Beach, FL (US)

( * ) Notice: Subject to any disclaimer, the term of this patent is extended or adjusted under 35 U.S.C. 154(b) by 210 days.

(21) Appl. No.: 17/244,307

(22) Filed: Apr. 29, 2021

(65) Prior Publication Data

US 2021/0244472 A1 Aug. 12, 2021

Related U.S. Application Data

(63) Continuation of application No. 15/957,085, filed on Apr. 19, 2018, now Pat. No. 11,109,912.
(Continued)

(51) Int. Cl.
*A61B 18/24* (2006.01)
*A61B 90/00* (2016.01)
(Continued)

(52) U.S. Cl.
CPC ............ *A61B 18/24* (2013.01); *A61B 18/245* (2013.01); *A61B 90/04* (2016.02);
(Continued)

(58) Field of Classification Search
CPC ....... A61B 18/24; A61B 90/04; A61B 18/245; A61B 2090/049; A61B 2017/00057;
(Continued)

(56) References Cited

U.S. PATENT DOCUMENTS 5,366,456 A 11/1994 Rink et al.
5,454,807 A 10/1995 Lennox et al.
(Continued)

OTHER PUBLICATIONS

Hutchens et al., "Hollow Steel Tips for Reducing Distal Fiber Burn Back During Thulium Fiber Laser Lithotripsy", Journal of Biomedical Optics 18(7), 078001 (Jul. 2013).
International Preliminary Examination in corresponding PCT application PCT/US2018/028285 dated Oct. 31, 2019.

*Primary Examiner* — Shirley X Jian
(74) *Attorney, Agent, or Firm* — Bacon & Thomas, PLLC

(57) ABSTRACT

A side-firing laser system with a standoff catheter includes an optical fiber configured to emit therapeutic laser radiation in a direction generally transverse to an axis of the fiber; and a catheter through which the optical fiber is inserted during a surgical procedure. The catheter includes a transparent end section through which the therapeutic laser radiation passes to vaporize tissue outside the catheter, an open distal end to permit exit of irrigation fluid from the catheter, and an opening in a side of the end section, the opening having dimensions that are approximately equal to or less than cross-sectional dimensions of the therapeutic laser radiation. When the fiber is moved to a position at which the therapeutic laser radiation passes through the opening, the laser radiation causes coagulation or vaporization of tissues.

16 Claims, 8 Drawing Sheets

Related U.S. Application Data

(60) Provisional application No. 62/487,131, filed on Apr. 19, 2017.

(51) Int. Cl.
*A61B 17/00* (2006.01)
*A61B 18/00* (2006.01)
*A61B 18/22* (2006.01)

(52) U.S. Cl.
CPC .............. *A61B 2017/00057* (2013.01); *A61B 2017/00907* (2013.01); *A61B 2018/00023* (2013.01); *A61B 2018/00511* (2013.01); *A61B 2018/00547* (2013.01); *A61B 2018/00601* (2013.01); *A61B 2018/00607* (2013.01); *A61B 2018/00625* (2013.01); *A61B 2018/2244* (2013.01); *A61B 2018/2272* (2013.01); *A61B 2018/2277* (2013.01); *A61B 2090/049* (2016.02); *A61B 2218/002* (2013.01)

(58) Field of Classification Search
CPC ........... A61B 2017/00907; A61B 2018/00023; A61B 2018/00511; A61B 2018/00547; A61B 2018/00601; A61B 2018/00607; A61B 2018/00625; A61B 2018/2244; A61B 2018/2272; A61B 2018/2277; A61B 2218/002
See application file for complete search history.

(56) References Cited

U.S. PATENT DOCUMENTS

| | | | |
|---|---|---|---|
| 5,476,461 A * | 12/1995 | Cho | A61B 18/24 606/17 |
| 5,487,740 A * | 1/1996 | Sulek | A61B 18/28 606/17 |
| 6,802,838 B2 | 10/2004 | Loeb et al. | |
| 7,909,817 B2 | 3/2011 | Griffin et al. | |
| 8,858,542 B2 | 10/2014 | Peng et al. | |
| 9,678,275 B1 | 6/2017 | Griffin | |
| 11,109,912 B2 * | 9/2021 | Brown | A61B 18/24 |
| 2008/0188843 A1 | 8/2008 | Appling et al. | |
| 2008/0292255 A1 | 11/2008 | Stevens et al. | |
| 2009/0248004 A1 * | 10/2009 | Altshuler | A61B 18/203 606/33 |
| 2010/0016845 A1 * | 1/2010 | Hanley | G02B 6/264 606/15 |
| 2011/0082450 A1 | 4/2011 | Melsky et al. | |
| 2011/0118715 A1 * | 5/2011 | Zerfas | G02B 6/34 606/15 |
| 2014/0135715 A1 * | 5/2014 | Lambert | A61B 18/24 606/15 |
| 2017/0042618 A1 | 2/2017 | Brown | |
| 2017/0128134 A1 * | 5/2017 | Pinnow | A61B 18/24 |
| 2018/0049806 A1 * | 2/2018 | Yu | A61B 18/22 |
| 2018/0303548 A1 * | 10/2018 | Brown | A61B 90/04 |
| 2021/0244472 A1 * | 8/2021 | Brown | A61B 18/245 |
| 2021/0330383 A1 * | 10/2021 | Griffin | G02B 6/0003 |

* cited by examiner

SIDE-FIRE LASER SYSTEM WITH STAND-OFF CATHETER, STANDOFF CATHETER, AND METHOD OF USING SURGICAL LASER TO ACHIEVE BOTH TISSUE VAPORIZATION AND RAPID COAGULATION TO PREVENT OR HALT BLEEDING

This application is a continuation of U.S. patent application Ser. No. 15/957,085, filed Apr. 19, 2018, which claims the benefit of U.S. Provisional Patent Appl. Ser. No. 62/487,131, filed Apr. 19, 2017, each of which is incorporated herein by reference.

BACKGROUND OF THE INVENTION

Field of the Invention

The invention relates to field of laser surgery, and in particular to systems and devices for delivering radiation to a tissue during a treatment procedure involving tissue vaporization, such as benign prostate hyperplasia (BPH) treatment or kidney stone removal, as well as to a laser surgery method.

The systems and devices of the invention involve side firing laser arrangements that are used with a standoff catheter to prevent contact between the laser fiber output surface and the tissue in order to reduce fiber degradation and allow extended use or reuse of the fiber. The standoff catheter includes a passage for insertion of the fiber, and through which irrigation fluid is caused to flow. In addition, the standoff catheter is adapted to facilitate both tissue vaporization and coagulation when used with the method of the invention.

The method of the invention allows the same laser delivery system or device to be selectively switched between tissue vaporization and coagulation, without having to withdraw the optical fiber from the patient, by substituting heavy water or a heavy water based mixture for a conventional water-based solution when coagulation is required, thereby improving treatment outcomes and patient safety.

1. DESCRIPTION OF RELATED ART

1a. Side Firing Surgical Laser Systems and Devices

A variety of devices and methods have previously been proposed to prevent contact between tissues or debris during surgical laser procedures involving cutting or destruction of tissues by vaporization. Tissue vaporization procedures inherently produce debris, which can accumulate on the fiber and cause degradation of the fiber. In addition, the need for an operator to position the fiber in close proximity to the fiber will frequently result in at least momentary contact between the tissue and fiber, which enhances fiber erosion and can cause flashes that interfere with the operator's view of the treatment site and fiber position.

For procedures involving end firing laser fibers, the inventor has proposed various resilient, generally cylindrical caps that are secured at least temporarily to the fiber and serves as a stand-off, allowing the fiber tip to be positioned in close proximity to the tissue without contact. The caps also serve to protect the scope during insertion, while being thin enough so as not interfere with fluid flow past the fiber. Examples of such caps are disclosed in the inventor's U.S. Provisional Patent Appl. Ser. No. 62/465,407, filed Mar. 1, 2017, which is incorporated herein by reference in its entirety.

For side-firing lasers, protection of the fiber has conventionally involved use of a transparent cap that is permanently affixed to the fiber, and through which the laser if fired, combined with an external tube or sleeve that enables flow of irrigation fluid past the fiber tip. The irrigation fluid is conventionally an aqueous solution such as saline, which is used to cool the fiber and flush debris away from the fiber.

An example of a side-firing surgical laser system that is commonly used is the commercially available Moxy™ system, described for example in U.S. Pat. No. 8,858,542, in which the optical fiber is surrounded by a protective jacket assembly made up of a body tube assembly and tip cap assembly. The tip cap assembly includes an internal fiber jacket and an external body tube with a body tube channel defined therebetween, and the tip cap assembly includes an inner cap member and an outer cap member defining a cap irrigation channel therebetween. The cap irrigation channel and the body tube channel cooperatively define an internal irrigation channel through which irrigation fluid in the form of a saline solution is directed to cool the fiber tip.

Unlike the approach taken by the standoff disclosed in the inventor's U.S. Provisional Patent Appl. Ser. No. 62/465,407, cited above, the Moxy™ system requires permanently affixed caps that cannot be replaced and that offer only a single window through which the laser is directed. Because the caps are permanently affixed, accumulation of debris on the inner and outer caps, and consequent degradation or increases in attenuation, can only be avoided by frequent cleaning of the cap, and/or frequent replacement of the entire fiber/cap arrangement, which results in high cost and extended treatment times, especially for procedures involving large glands.

An alternative to the Moxy™ system is the dual-cap system was proposed in U.S. Pat. No. 7,909,817, which was based on an even earlier fluid-cooled side-firing system disclosed by the inventor in a U.S. patent application filed in 1993. This system also involves a cap permanently affixed to the fiber and a "secondary capsule" surrounding the permanently affixed cap and separated therefrom by an index matching irrigation fluid channel, with side-firing of the laser being achieved by a beveled surface at the tip of the fiber. Unlike the Moxy™ system the primary and secondary caps are both made of a transparent material through which the laser is directly fired, without the need for windows. While simpler than the Moxy™ system, however, this alternative system is still relatively complex and expensive because the entire fiber system needs to be cleaned or replaced as debris accumulates on the secondary cap and/or as degradation or erosion occurs. An illustration of this system is provided in FIG. 1 [FIG. 2b of U.S. application Ser. No. 15/234,455, filed Aug. 11, 2016, incorporated by reference in its entirety].

Another alternative to the Moxy™ system is the system disclosed in U.S. Pat. No. 6,802,838 (the Trimedyne system), which utilizes a catheter that is crimped to the fiber or secured thereto by an insert, and that includes a window through which the laser is fired, as well as multiple ports for fluid input and debris removal. Because the catheter is fixed to the fiber, the Trimedyne system suffers at least the same cost and treatment-time disadvantages as the Moxy™ system, including the disadvantage of providing only a single window for emission of the radiation.

A side-firing design that eliminates the need to clean or replace the entire fiber system due to debris accumulation by providing a removable or replaceable outer tube through which the laser can be fired was disclosed by the inventor in U.S. patent application Ser. No. 15/234,455, filed Aug. 11, 2016, and incorporated herein by reference. which show various designs for a disposable or removable sleeve that can be fitted over the side firing laser and/or an outer tube of a system such as the Moxy™ system or the system disclosed in U.S. Pat. No. 7,909,817, enabling debris accumulation on or damage to the outer tube to be addressed by simply removing and replacing the sleeve, without the need to replace the fiber itself, or to clean the fiber and Moxy™ cap(s), during a surgical procedure. Examples of this system are illustrated in FIGS. 2-6.

The present invention provides further variation of the designs disclosed in U.S. patent application Ser. No. 15/234,455, in which the outer sleeve is in the form of a catheter that, unlike the catheter of the Trimedyne system, is modified so that it can be easily removed and replaced without having to also dispose of the fiber, and which does not require a single window through which the laser must be fired during a tissue cutting or vaporization procedure, allowing the fiber to be freely rotated within the catheter and thereby limiting damage to any one area of the catheter while still preventing contact between the fiber and the tissue being treated, and yet that also still provides for continuous fluid flow over the fiber.

The stand-off catheter of the invention, like the disposable or replaceable sleeves disclosed in application Ser. No. 15/234,455, may be used with any of a variety of different side-firing laser fiber configurations, including fibers with beveled side-fire tips that utilize total internal reflection to direct the laser in a transverse or radial direction, fibers with beveled tips that utilize a reflector or reflective coating rather than total internal reflection to direct the laser beam, and fibers without beveled tips that are converted into side-firing arrangements by attaching a reflector to the end of the fiber at an appropriate angle, or including the reflector in a cap affixed to the fiber.

The stand-off catheters of the invention are especially suitable for use with a surgical laser method that adds a surprising capability to conventional tissue vaporization methods. The surprising capability is that, when heavy water (D2O) rather than ordinary water (H2O) is used as an irrigation fluid, the heavy water suppresses vaporization of tissues, so that application of the laser instead causes cauterization. This permits stoppage of bleeding without the need to withdraw the fiber and use conventional methods of coagulation, such as electro-cauterization, by switching between ordinary and heavy water. It also allows rapid coagulation because the effect works even at high power.

1a. Use of Heavy Water to Enable Use of Surgical Laser to Switch Between Tissue Vaporization and Coagulation U.S. Provisional Patent Appl. Ser. No. 62/252,477, filed Nov. 7, 2015, by Dr. Douglas Pinnow, proposed the novel concept of using heavy water as an irrigation fluid for the purpose of reducing attenuation of the laser during vaporization, in order to potentially enhance vaporization efficiency during procedures involving tissue vaporization. It was believed that this would decrease treatment time because more energy would reach the tissue as a result of the lower attenuation.

The present inventor has discovered, however, that the heavy water actually has the effect of preventing tissue vaporization, so that when the laser is directed to an area where bleeding is occurring, coagulation occurs. The inventor is unaware of any related art disclosing the concept of using heavy water as an irrigation fluid to cause coagulation rather than vaporization when a surgical laser is directed at the tissue.

As used herein, the terms "water," "aqueous solution," or "saline" refer to irrigation fluids that contain ordinary water made up of hydrogen and oxygen atoms with the chemical formula $H_2O$, while the terms "heavy water" or "heavy water solution" refer to irrigation fluids that contain a form of water made up of hydrogen isotopes with an extra neutron and oxygen, and with the chemical formula $D_2O$.

SUMMARY OF THE INVENTION

The invention provides an improved side-firing laser system in which a catheter is configured to serve as a standoff that prevents contact between the laser and tissues, thereby providing protection for the fiber. In addition, the standoff catheter is adapted to not only enable tissue vaporization through the catheter when an aqueous solution is supplied through the catheter as an irrigation fluid, but also tissue coagulation when heavy water is substituted as the irrigation fluid.

The standoff catheter extends the useful life of a side-firing fiber or fiber/cap arrangement, eliminating the need for frequent cleaning or replacement. It may be used with any of a variety of side-fire configurations, including configurations with beveled fiber tips and systems with caps that are permanently affixed by adhesives, welding, or crimping.

The use of heavy water to enable coagulation of tissues using the same laser system that is used for tissue vaporization has application to systems and procedures other than those utilizing the standoff catheter system of the invention, or side-firing laser systems in general, and is itself a novel aspect of the invention that may be applied to a variety of laser surgical procedures and equipment, including those that use end-firing lasers.

In a preferred embodiment of the invention, the standoff catheter includes a generally cylindrical catheter tip that is fixed to the catheter tube and that is made of a transparent material such as quartz or sapphire, through which the laser is directed to vaporize tissues. An open end of the standoff catheter permits passage of irrigation fluid, such as a water-based saline solution or heavy water, which flows through the catheter to provide a cooling effect, although it will be appreciated by those skilled in the art that the open end of the standoff catheter may be replaced or supplemented by one or more fluid exit openings, grooves, or channels in a side of the standoff catheter.

As an adaptation to facilitate use of the standoff catheter, at least one small aperture or opening is provided in or near the catheter tip, where the aperture is dimensioned to allow passage of the laser beam for purpose of coagulation or vaporization while limiting fluid flow through the aperture. The hole is small enough to prevent tissue debris from entering and contacting the laser fiber. When lasing, no water or fluid flows out or in due to the steam bubble or air channel formed. If tiny tissue debris does flow in, the water forces it out the end of the catheter.

In order to enable the dual vaporization/coagulation functions of the system and method, the fiber is movable within the catheter to a position in which the laser beam is transmitted through the transparent material and/or through the beam aperture or opening of the catheter for tissue vaporization or for tissue coagulation. In order to achieve coagulation, heavy water or a heavy water based solution or mixture is substituted for the conventional water based solution. The heavy water prevents tissue vaporization when the laser beam is fired, eliminating charring and the need for other methods of stopping bleeding, such as electro-cauterization.

Because the beam aperture or opening in the standoff catheter of the preferred embodiment is sized to permit fluid flow, as the laser beam passes through the opening, when heavy water is used, the heavy water flows to the tissue and keeps the tissue from vaporizing, e.g., coagulation. However, when the conventional water based solution is used, the beam aperture or opening is sized so that an air passage is formed by heating and vaporization of any water in its path, allowing unattenuated passage of the laser beam to the tissue and consequent maximum energy transmission by insulating the heated tissue. That is, since water is highly absorbent to infrared radiation, e.g., 1470 nm wavelength, the laser beam vaporizes the water to insulate tissue, whereas since heavy water transmits infrared radiation, it allows the cooling of the tissue, e.g., coagulation. If the end of the standoff catheter is open, a flange or stopper may be provided at the end of the catheter to facilitate alignment of the radiation beam with the opening during coagulation and/or vaporization.

The step of switching to heavy water or a heavy water based solution or mixture in order to achieve coagulation is not limited to applications involving the standoff catheter described herein, but rather may be used in any surgical laser application where coagulation might be required, including applications that utilize end firing fiber configurations.

In addition, instead of simply switching irrigation fluids when coagulation is required, it is possible to continue to use the conventional water based solution as one irrigation fluid while switching another irrigation fluid to heavy water in applications involving multiple irrigation sources, for example by continuing to use conventional water for fiber irrigation and switching the scope irrigation to heavy water or a heavy water based solution or mixture.

DETAILED DESCRIPTION OF THE PREFERRED EMBODIMENTS

Throughout the following description and drawings, like reference numbers/characters refer to like elements. It should be understood that, although specific exemplary embodiments are discussed herein there is no intent to limit the scope of present invention to such embodiments. To the contrary, it should be understood that the exemplary embodiments discussed herein are for illustrative purposes, and that modified and alternative embodiments may be implemented without departing from the scope of the present invention.

As shown in FIGS. 7(a) thru 7(d), a surgical laser fiber 100 includes a transparent cap or tube 101 that includes a reflector or reflective surface 102 for directing laser energy in a generally radial direction with respect to an axis of the fiber. The fiber and cap arrangement of this embodiment forms no part of the present invention, and is by way of example only. Those skilled in the art will appreciate that any of the fiber/cap arrangements disclosed in FIGS. 2-7 or in copending U.S. patent application Ser. No. 15/234,455, or other side-firing tip and/or cap configurations, may be substituted for the arrangement illustrated in FIGS. 7(a) thru 7(d).

Instead of a conventional outer tube or catheter, however, FIGS. 7(a) thru 7(d) show a standoff catheter 104 constructed in accordance with the principles of the invention. Although the term "catheter" is used herein, it will be appreciated that the catheter 104 may be referred to as an introducer or sleeve, and is a generally cylindrical structure that is inserted into the patient via a laser endoscope, cystoscope, or resectoscope, and through which the fiber inserted to the treatment site.

Figure 1:
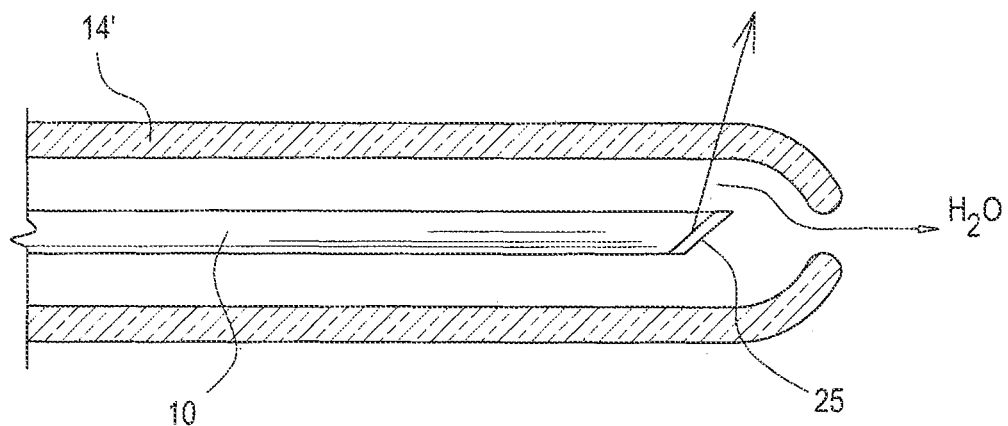
FIG. 1 is an illustration of a previously-proposed side-fire laser fiber arrangement.
Figure 2:
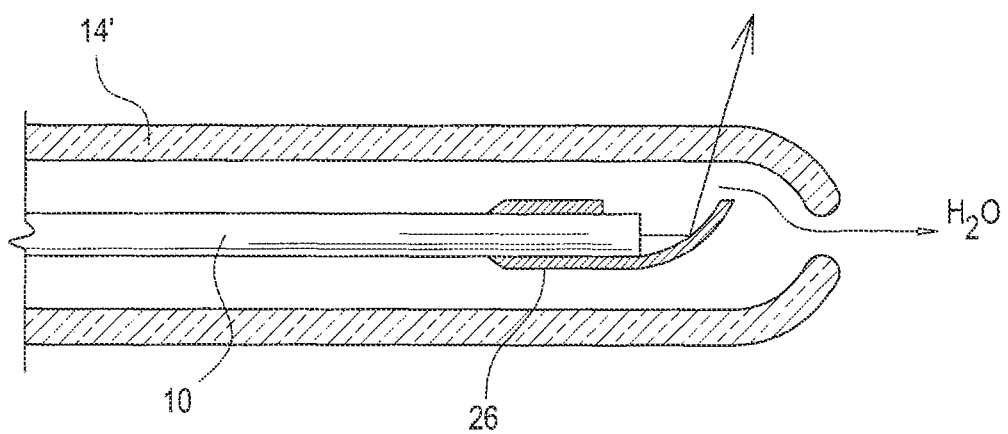
FIGS. 2-6 show side-fire laser systems disclosed in the inventor's U.S. patent application Ser. No. 15/234,455.
Figure 3:
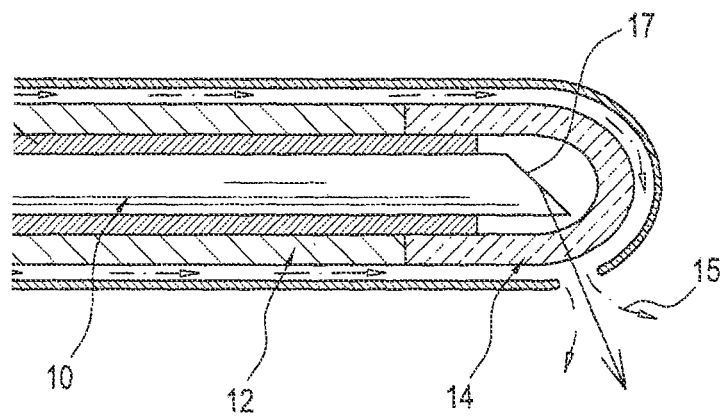
Figure 4:
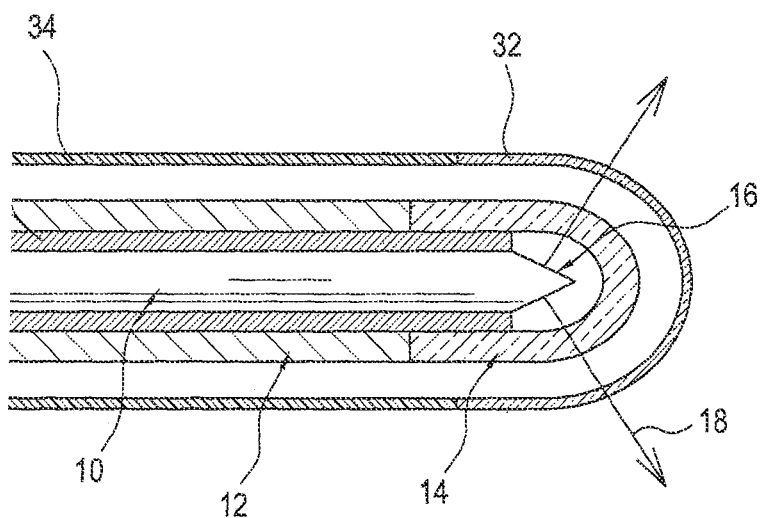
Figure 5:
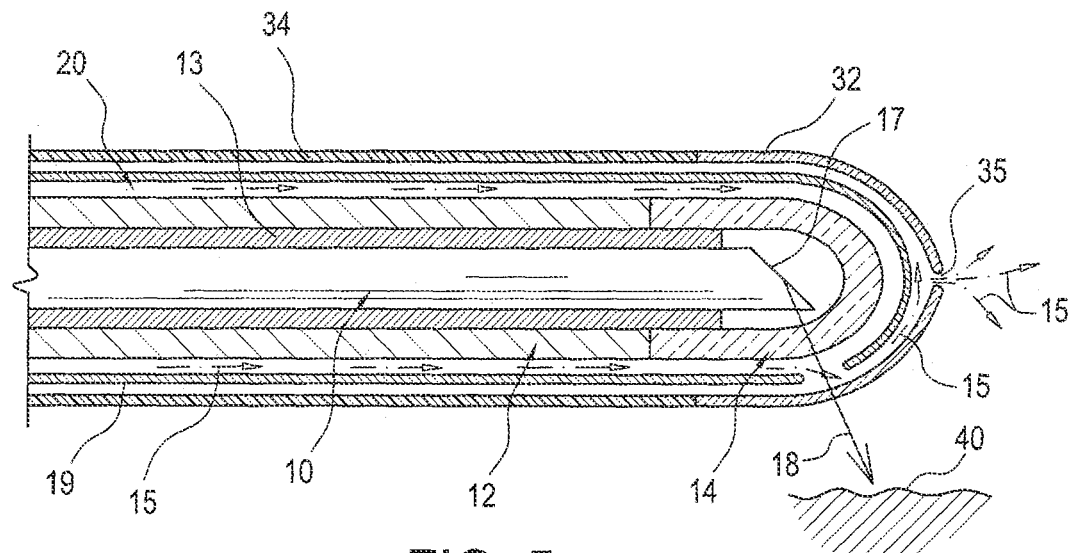
Figure 6:
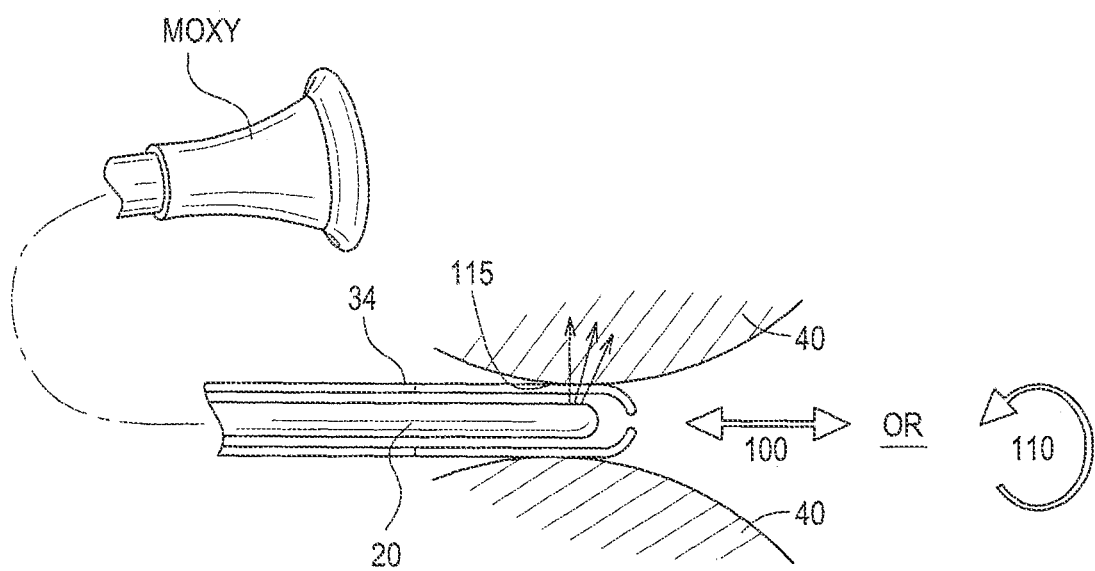
Figure 7A:
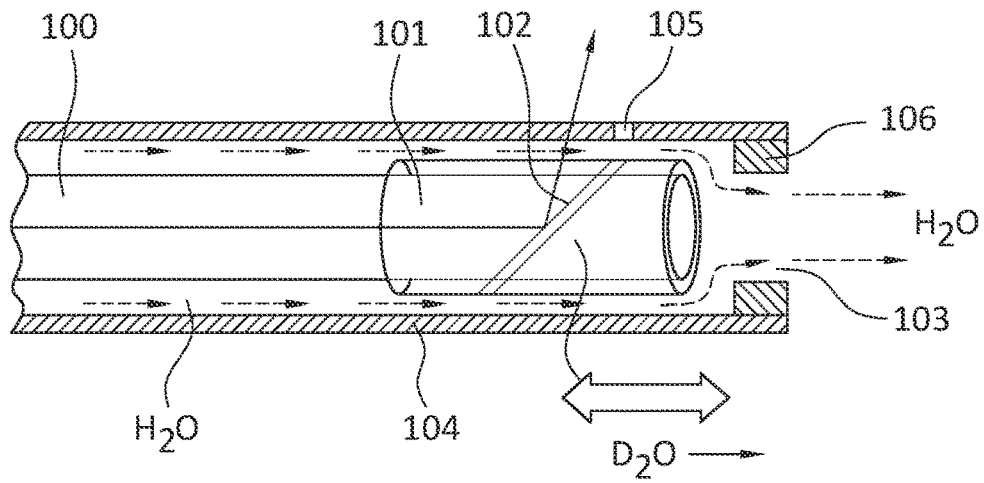
FIGS. 7(a), 7(b), 7(c), and 7(d) are side views of a standoff catheter constructed in accordance with the principles of a first preferred embodiment of the invention, and which is arranged to provide both tissue vaporization and coagulation.

At least the generally cylindrical distal end section of the standoff catheter 104 is made of a transparent material through which the laser is directed to vaporize tissues, as illustrated in FIG. 7(a). In this example, the transparent material of the standoff may be any of a variety of transparent materials, such as sapphire or quartz. The standoff catheter has an open end 103 that permits passage of irrigation fluid, such as a water-based saline solution or heavy water, which is caused to flow through the catheter and thereby provide a cooling effect. The solution is preferably index matched to minimize attenuation. Because the distal end of the standoff catheter emits transparent to laser radiation, the laser can be fired in any direction through the catheter and along the length of the distal end section, reducing radiation or heat damage at any one location.

As adaptations to use in a method that permits switching between vaporization and coagulation modes, the standoff catheter of this embodiment includes a fiber position stopper or flange 106 at or near an end of the catheter, and an aperture or opening 105 situated a predetermined distance from the stopper 106.

Figure 7B:
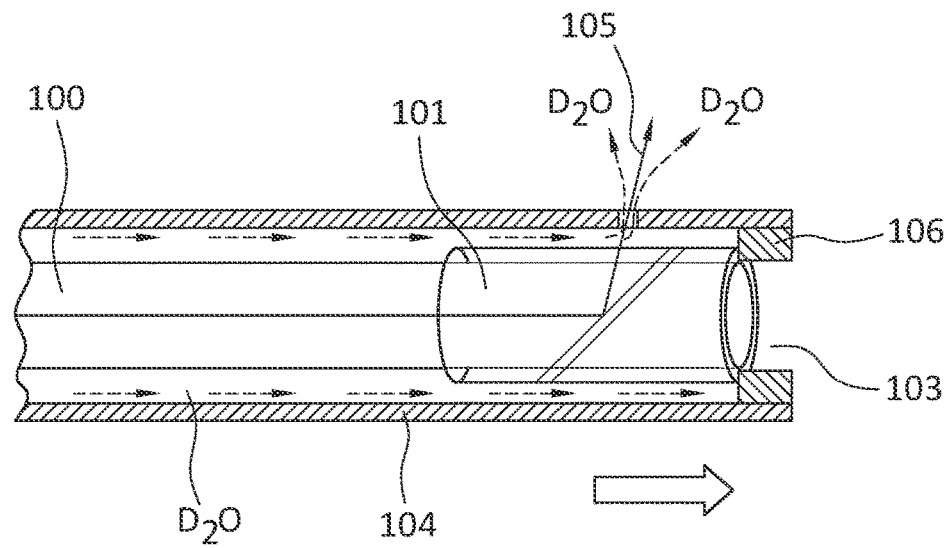

The aperture or opening 105 can be used either when the water-based saline solution or the heavy water is used. While it is understood that the standoff catheter can emit radiation along any length, a stopper or flange 106 is provided to align the laser beam with the aperture or opening 105. As illustrated in FIG. 7(b), when heavy water is used, the opening has a size that is too small for a substantial amount of water to pass, but rather has dimensions in the order of the beam width of the laser, i.e., just large enough to permit passage of most or all of the laser beam through the opening 105. For example, the opening can be sized 70-80% of the core size of the fiber, e.g., between 1-1000 microns, and preferably between 200-600 microns, but not limited thereto, since the size is determined as a trade-off between efficiency of radiating the tissue, Fresnel refractions, fluid flow, and other factors. While the opening is not primarily intended for cooling or flushing of debris, but solely to provide passage for the laser when water, heavy water, or another liquid is used as an irrigation fluid, it is appreciated that when a stopper is used, water or the heavy water is able to be pushed through the opening, if necessary. Because the laser does not pass through the catheter when in the position shown in FIG. 7(b), it is not subject to Fresnel reflections and consequent attenuation.

Even though the laser reaches the tissue with minimal attenuation, the presence of heavy water prevents vaporization of the tissue. Instead, any blood in the tissue is caused to coagulate, without charring.

The stopper 106 facilitates positioning of the fiber tip relative to the opening 105 during radiation. In order to achieve axial alignment, the operator simply needs to move the fiber relative to the catheter so that the end of the fiber cap abuts against the stopper, at which time laser reflector is aligned with the opening. An appropriate fiber lock (not shown) such as the luer lock of the inventor's U.S. patent application Ser. No. 14/218,407, filed Mar. 18, 2014, and Ser. No. 14/520,551, filed Oct. 22, 2014, each of which is incorporated herein by reference, may be provided at the proximal end of the fiber, with or without a fine adjustment mechanism, to facilitate movement of the fiber relative to the catheter and to lock the fiber at a desired position with respect thereto.

Although not shown, more than one opening or aperture 105 may be included in the catheter in case the original opening becomes worn, for example by distributing the apertures at different angles around the circumference of the catheter. Alternatively, in case of excess wear of the standoff catheter, the fiber could simply be withdrawn from the worn catheter and re-inserted into a new catheter.

In order to use the standoff catheter of FIGS. 7(a) and 7(b), a surgical laser procedure is carried out in conventional fashion using water or saline solution, and causing the laser beam to be pass through the transparent material of the catheter to vaporize tissue or the fiber tip is moved to a position where the end of the fiber abuts the stopper 106 so that the laser is caused to pass through the opening 105. When tissue coagulation becomes necessary, however, heavy water is substituted for the water or saline, at which time coagulation rather than vaporization occurs.

Figure 7E:
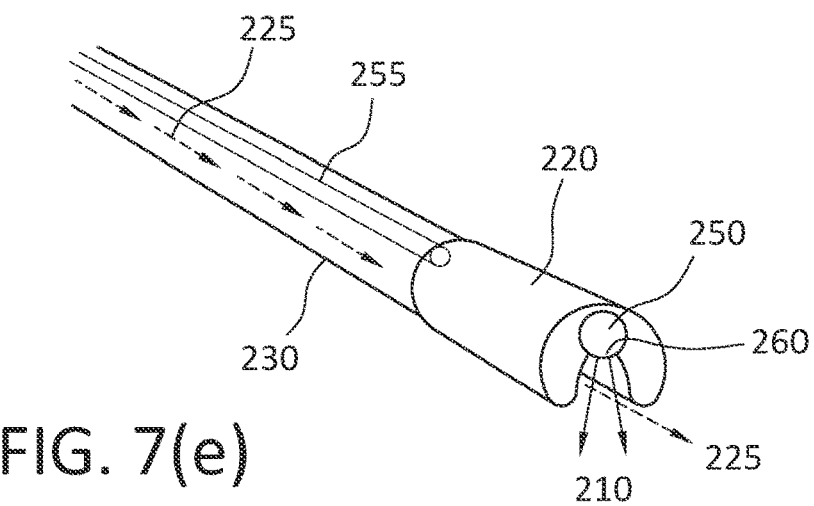
FIG. 7(e) is a side view of a variation of the standoff catheter of FIGS. 7(a) and 7(b) in which the fluid exit opening is provided in a side of the standoff catheter tip.
Figure 7D:
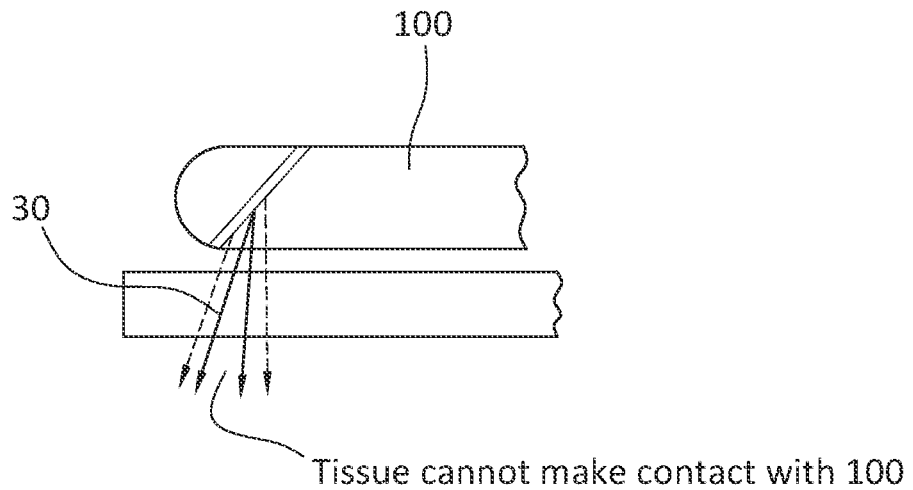
Figure 7C:
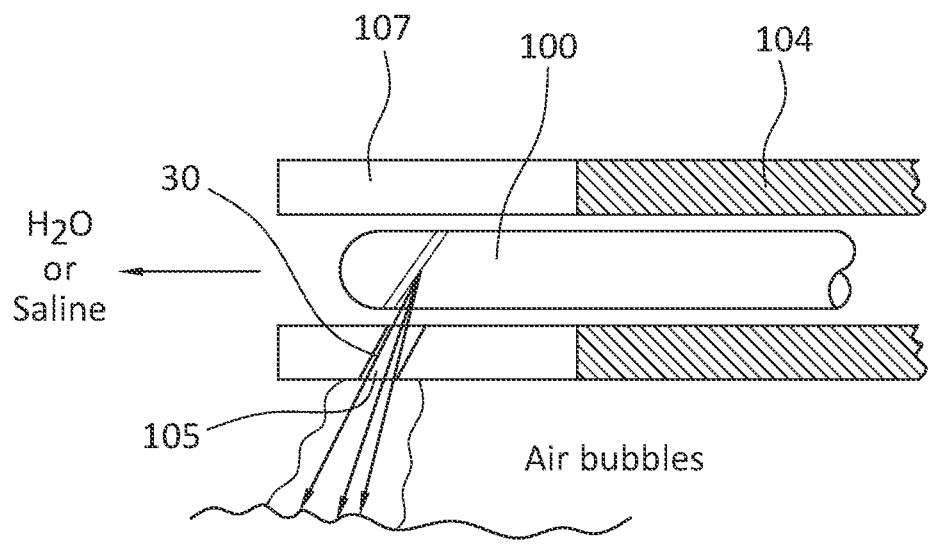

As seen in FIG. 7(c), when water or saline solution is used and the laser beam 30 is aligned with the aperture or opening 105, any liquid in the opening 105 or present in the direct path of the treatment radiation beam between the catheter and the tissue during lasing is heated and turned to steam by the laser, thereby forming an air channel from the catheter to the tissue to minimize absorption of the laser beam. Additionally, similarly as discussed above, because the laser does not pass through the catheter when in the position shown in FIG. 7(c) (or FIG. 7(b)), it is not subject to Fresnel reflections and consequent attenuation. Additionally, optionally, the standoff catheter 104 can include a transparent material 107.

In either embodiment using conventional water or heavy water, it is appreciated that as illustrated in FIG. 7(d), the laser fiber 100 cannot make contact with the tissue, since such contact would adversely affect the vaporization or coagulation of the tissue. It is appreciated that the use of the aperture or opening 105 prevents the Fresnel reflection and consequent attenuation so that more power can be used to vaporize or coagulate the tissue, e.g., up to 10-20% of additional power.

In a variation of the embodiment illustrated in FIGS. 7(a) and 7(d), the open end of the standoff catheter is replaced by a transverse opening formed by a groove in the transparent tip 220 of catheter tube 230, into which fiber 255 is inserted, as shown in FIG. 7(e). Irrigation fluid 225 supplied through the catheter tube 230 exits the tube 230 and flows through the groove past the transparent side firing tip 250, which is situated on one side of the groove and may include an opening 260 corresponding to the opening 105 described above. As described above, the laser output 210 may be through the transparent tip 220 or through the opening 260 depending on fiber tip position and whether the irrigation fluid is conventional or heavy water based. Alternatively, the irrigation fluid may exit the catheter or catheter tip through multiple outlets or ports in a side and/or end surface of the catheter tip.

It will be appreciated that it may be possible to axially position the fiber tip relative to the opening without the use of a physical stopper and the distal end of the catheter. In addition, coagulation will occur whenever heavy water and an appropriate laser is used, and therefore the method of switching between heavy water and ordinary water or saline during a procedure to achieve coagulation may be used with arrangements other than the standoff catheter arrangements illustrated in FIGS. 7(a) to 7(e).

Figure 10:
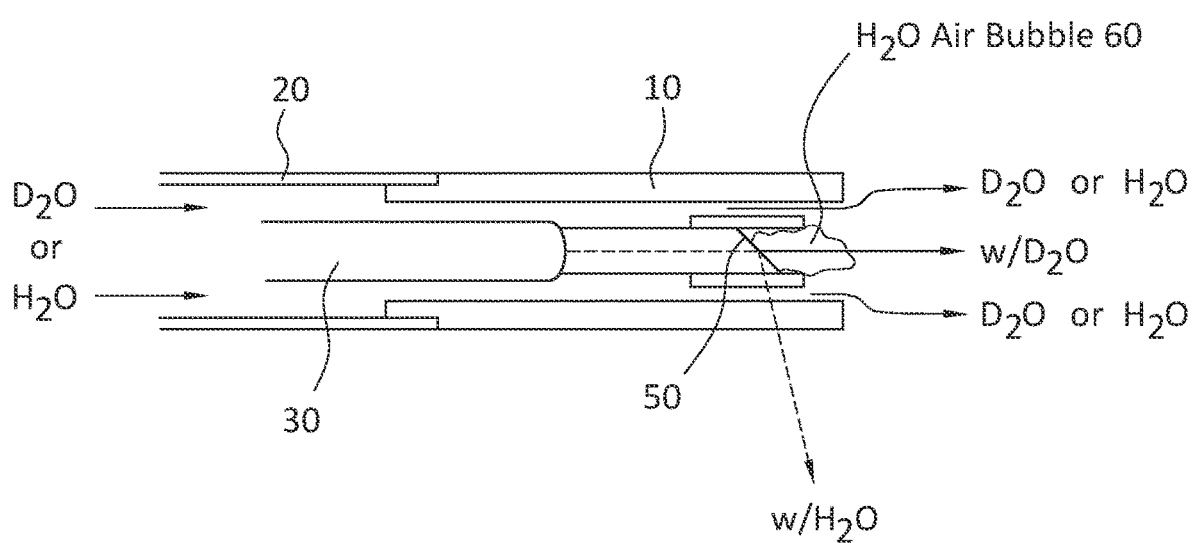

For example, it may be possible to eliminate the inner cap and utilize different absorption properties of water and heavy water to switch between radial and axial emission from a beveled fiber tip. Because water is highly absorbent to laser energy at 1470 nm, the water in front of the beveled tip will vaporize and cause total internal reflection of the laser, as illustrated in FIG. 10, causing radial emission through a tube secured to the catheter and made, by way of example and not limitation, of a transparent material such as quartz or sapphire. On the other hand, heavy water transmits the laser energy, e.g., at a wavelength of 1470 nm, and therefore the laser beam is transmitted axially when heavy water is used. As in the preferred embodiment described above, water is used for tissue vaporization and heavy water for coagulation.

Figure 8:
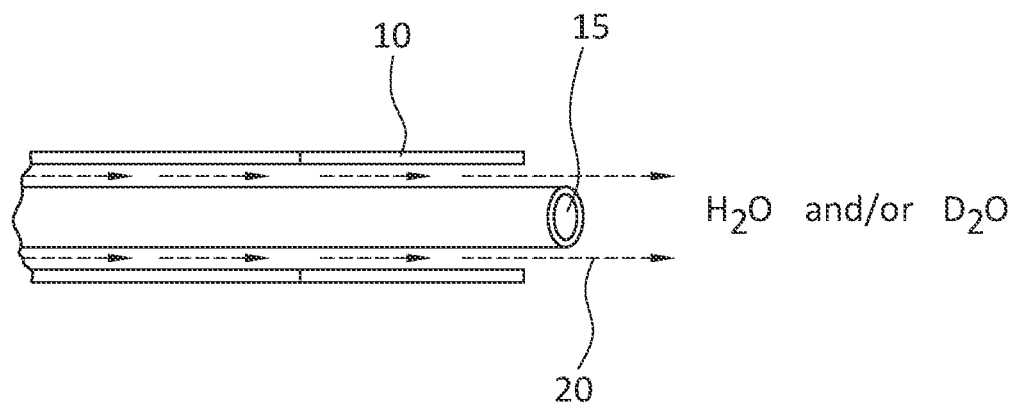
FIGS. 8-10 are side views showing variations of the invention, in which water and heavy water are applied to different end and side firing laser arrangements.
Figure 9:
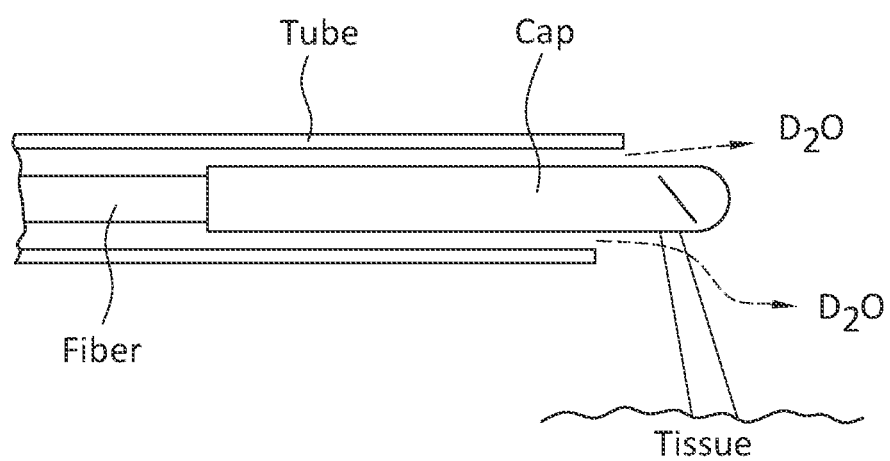

FIGS. 8, 9, and 10 show the use of water and heavy water with more conventional axial and side fire arrangements. FIG. 8 shows an end fire arrangement, in which the fiber may be a bare fiber or provided with a cap or tube of the type disclosed in PCT/US2017/031091, filed May 4, 2017, incorporated herein by reference in its entirety, and inserted through an introducer 10 that permits passage of water for vaporization and heavy water for coagulation.

FIG. 9 illustrates a side-fire arrangement where the fiber may be extended beyond the tube or catheter in order to eliminate Fresnel reflections, to clean the fiber, or to fire through the higher concentration of $D_2O$ in front of the tube's irrigation output.

FIG. 10 is a side-fire arrangement having an angled reflector or beveled fiber tip, and tube through which water for tissue vaporization and heavy water for coagulation are introduced. As seen in FIG. 10, the reflective bevel does not require a cap to maintain air for total internal reflection, but when the infrared laser is fired, a steam bubble is maintained on the bevel surface.

Figure 11:
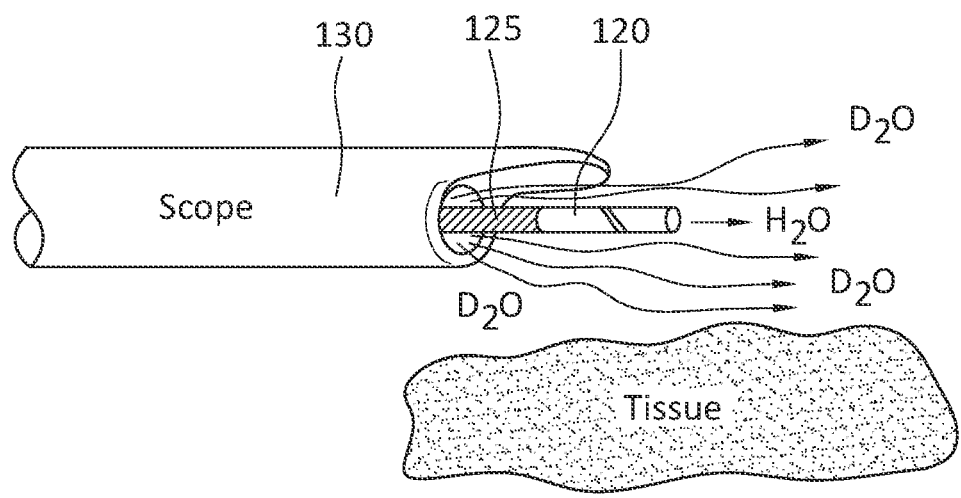
FIG. 11 illustrates a variation of the preferred method of switching from tissue vaporization to coagulation, in which scope irrigation is switched from a conventional water-based solution to a heavy water or a heavy water solution or mixture while the conventional water-based solution continues to be used for fiber irrigation.

Those skilled in the art will appreciate that the invention is not limited to use of heavy water by itself, and that solutions or mixtures of heavy water, including mixtures of heavy water and ordinary water, may also have the desired coagulation effect. In addition, instead of simply switching irrigation fluids when coagulation is required, it is possible to continue to use the conventional water based solution as one irrigation fluid while switching while switching another irrigation fluid to heavy water in applications involving multiple irrigation sources, for example by continuing to use conventional water for fiber irrigation and switching the scope irrigation to heavy water or a heavy water based solution or mixture. For example, as shown in FIG. 11, a conventional water-based irrigation fluid may be supplied through a standoff catheter tip 120, such as the one illustrated in FIGS. 7(*a*) and 7(*d*), after insertion of the catheter tube 125 into a scope 130, while at the same time also supplying a conventional water-based irrigation fluid through the scope 130. When it is desired to coagulate rather than vaporize tissue, instead of replacing the conventional water-based irrigation fluid supplied to the standoff catheter tip 120, only the water-based irrigation fluid in the scope is changed to heavy water or a heavy water solution or mixture that causes coagulation. The irrigation fluid can then be switched back to conventional fluid in order to continue the vaporization procedure, if desired.

We claim:

1. A laser delivery system for delivering treatment radiation from a laser to a tissue, comprising:
   an optical fiber configured to emit the treatment radiation in a direction generally transverse to an axis of the fiber; and
   a protective structure surrounding a distal end of the fiber,
   wherein the protective structure has an irrigation fluid exit opening to permit exit of irrigation fluid from the protective structure,
   wherein treatment radiation emitted by the optical fiber passes through the protective structure, and
   wherein liquid present in a direct path of the treatment radiation from the optical fiber through the protective structure to the tissue is heated and vaporized by the treatment radiation, thereby forming an air channel that minimizes absorption of the treatment radiation.

2. A laser delivery system as claimed in claim 1, wherein the protective structure further has at least one side opening in a side of the protective structure, the side opening having dimensions that are approximately equal to or less than cross-sectional dimensions of the treatment radiation to enable passage of said treatment radiation in said direction generally transverse to an axis of the fiber to treat tissue outside the protective structure, without permitting passage of said irrigation fluid or ingress of debris and without Fresnel reflections.

3. A laser delivery system as claimed in claim 2, wherein the treatment radiation is laser energy having a wavelength of 1470 nm.

4. A laser delivery system as claimed in claim 1, wherein the protective structure is an end of a catheter.

5. A laser delivery system as claimed in claim 1, wherein the protective structure and optical fiber are relatively movable or rotatable.

6. A laser delivery system as claimed in claim 1, wherein the protective structure is replaceable.

7. A laser delivery system as claimed in claim 1, wherein the protective structure is transparent.

8. A laser delivery system as claimed in claim 1, wherein the optical fiber has a beveled tip that causes the radiation to be emitted in the generally transverse direction.

9. A laser delivery system as claimed in claim 8, wherein the optical fiber has a transparent cap that is affixed to the distal end of the fiber.

10. A laser delivery system as claimed in claim 1, wherein the optical fiber has a reflector affixed to the end of the fiber to reflect the radiation in the generally transverse direction.

11. A laser delivery system as claimed in claim 1, wherein the optical fiber has a transparent cap that is affixed to the distal end of the fiber, the transparent cap including a reflector positioned to reflect the radiation in the generally transverse direction.

12. A laser delivery system as claimed in claim 1, wherein the protective structure is made of sapphire or quartz.

13. A surgical method that enables coagulation during laser surgery using a same laser system as is used to vaporize or cut tissues, comprising the steps of:
    directing laser radiation at a tissue through an optical fiber while using a water-based irrigation fluid to vaporize the tissue;
    selectively supplying heavy water or a heavy water solution or mixture as an irrigation fluid; and
    directing the laser radiation at the tissue through the optical fiber while supplying the heavy water or heavy water solution or mixture in order to cause coagulation.

14. The surgical method of claim 13, wherein the step of directing laser radiation at a tissue is implemented using a side-firing optical fiber system inserted into a standoff catheter, and further comprising the step of moving the distal end of the optical fiber from a position in which the laser radiation is fired through a transparent material of the catheter to a position in which the laser radiation is fired through an opening in the catheter, and firing the laser radiation through the opening upon supplying the heavy water or heavy water solution or mixture as the irrigation fluid.

15. The surgical method of claim 14, wherein the step of supplying the heavy water or heavy water solution or mixture includes the step of switching from the water-based irrigation fluid to the heavy water or heavy water solution or mixture.

16. The surgical method of claim 14, wherein during tissue vaporization the water-based irrigation fluid is supplied through both a scope and a catheter inserted into the scope, and wherein the step of supplying the heavy water or heavy water solution or mixture includes the step of supplying the heavy water or heavy water solution or mixture through the scope while continuing to supply the water-based irrigation fluid through at least the catheter.

\* \* \* \* \*